United States Patent
Simmons et al.

(10) Patent No.: US 11,685,899 B2
(45) Date of Patent: Jun. 27, 2023

(54) CELL CULTURE METHOD FOR MESENCHYMAL STEM CELLS

(71) Applicant: Mesoblast International Sàrl, Meyrin (CH)

(72) Inventors: Paul Simmons, Melbourne (AU); Colby Suire, New York, NY (US)

(73) Assignee: MESOBLAST INTERNATIONAL SARL, Meyrin (CH)

( * ) Notice: Subject to any disclaimer, the term of this patent is extended or adjusted under 35 U.S.C. 154(b) by 457 days.

(21) Appl. No.: 16/599,271

(22) Filed: Oct. 11, 2019

(65) Prior Publication Data

US 2020/0040303 A1    Feb. 6, 2020

Related U.S. Application Data

(63) Continuation of application No. 15/553,115, filed as application No. PCT/EP2016/054640 on Mar. 4, 2016, now abandoned.

(30) Foreign Application Priority Data

| Mar. 4, 2015 | (AU) | ................................ 2015900752 |
| Mar. 5, 2015 | (AU) | ................................ 2015900777 |

(51) Int. Cl.
    *C12N 5/0775*      (2010.01)

(52) U.S. Cl.
    CPC ........ *C12N 5/0662* (2013.01); *C12N 2500/99* (2013.01); *C12N 2501/11* (2013.01); *C12N 2501/115* (2013.01); *C12N 2501/135* (2013.01)

(58) Field of Classification Search
None
See application file for complete search history.

(56) References Cited

U.S. PATENT DOCUMENTS

| 2010/0261274 A1 | 10/2010 | Vodyanyk et al. |
| 2012/0177614 A1 | 7/2012 | Kido |
| 2012/0329087 A1 * | 12/2012 | Tsuchiya ............... C12N 5/0668 |
| | | 435/406 |
| 2015/0118748 A1 * | 4/2015 | Ra ........................ C12N 5/0667 |
| | | 435/325 |

FOREIGN PATENT DOCUMENTS

| EP | 2 545 928 A1 | 1/2013 |
| JP | 2008-148643 A | 7/2008 |
| WO | WO 2008/020815 A1 | 2/2008 |
| WO | WO 2011/159359 A2 | 12/2011 |

OTHER PUBLICATIONS

Meuleman et al., Eur. J. Haematol., 76:309-316 (2006) (Year: 2006).*
Jung et al., J. Tissue. Eng. Regen. Med., 6:391-403 (2012) (Year: 2012).*
Chase et al., Stem Cell Res. Ther. 1(8):1-11 (2010) (Year: 2010).*
Müller, I., et al, "Animal serum-free culture conditions for isulation and expansion of multipotent mesenchymal stromal cells from human BM", Cytotherapy (2006) vol. 8, No. 5, pp. 437-444.
International Search Report issued in connection with PCT International Application No. PCT/EP2016/054640.
Written Opinion of the International Searching Authority issued in connection with PCT International Application No. PCT/EP2016/054640.
Dec. 12, 2018 Office Action, issued in connection with U.S. Appl. No. 15/553,115.
Mar. 12, 2019 Response to the Dec. 12, 2018 Office Action issued in connection with U.S. Appl. No. 15/553,115.
Apr. 15, 2019 Second Office Action issued in connection with U.S. Appl. No. 15/553,115.

* cited by examiner

*Primary Examiner* — Michelle F. Paguio Frising
(74) *Attorney, Agent, or Firm* — John P. White

(57) ABSTRACT

The present disclosure relates to methods, cell culture medium and compositions that promote cell proliferation during fetal bovine serum free cell culture.

11 Claims, 11 Drawing Sheets

CELL CULTURE METHOD FOR MESENCHYMAL STEM CELLS

CROSS-REFERENCE TO RELATED APPLICATIONS

This application is a continuation of U.S. application Ser. No. 15/553,115, filed Aug. 23, 2017, which is a § 371 national stage of PCT International Application No. PCT/EP2016/054640, filed Mar. 4, 2016, claiming priority of Australian Patent Applications Nos. AU 2015900777, filed Mar. 5, 2015 and AU 2015900752, filed Mar. 4, 2015, the contents of each of which are hereby incorporated by reference into the application.

TECHNICAL FIELD

The present disclosure relates to methods, cell culture media and compositions that promote stem cell proliferation during fetal bovine serum (FBS) free cell culture.

BACKGROUND

Multipotent mesenchymal stem cells (MSC) have been proposed as an attractive candidate for therapeutic applications because of their high proliferation and differentiation potential as well as immunoregulatory and other beneficial properties (Caplan Ai (2007) J. Cell Physiol., 213, 341-347; Prockop DJ (2007) Clin Pharmacol Ther., 82, 241-243). Ex vivo propagation of sparse populations of mesenchymal stem cells (MSC) is often necessary for generating numbers suitable for therapeutic applications.

Conventional media used for isolating and expanding MSC consist of a defined basal medium (e.g. Dulbecco's modified Eagle's medium (DMEM) or α-modified minimum essential medium (α-MEM)) supplemented with fetal bovine serum because of its high content of stimulatory growth factors. Although these media are generally reported to support the proliferation of MSC for multiple passages, concerns have been raised because of the potential risks associated with fetal bovine serum (Dimarakis & Levicar (2006) Stem Cells., 24, 1407-1408; Marinello & Tonti (2007) Stem Cells., 25, 1603-1609). In particular, fetal bovine serum may contain harmful contaminants such as prion, viral and zoonotic agents, and can elicit immune reactions. Moreover, the poorly defined nature of fetal bovine serum, and its high degree of batch-to-batch variation, can cause inconsistencies in the growth-supporting properties of media, and thus make standardization of a cell production process difficult.

Human sourced supplements, such as human serum and platelet lysate, have been investigated as a replacement for fetal bovine serum. Human serum is not generally considered a suitable replacement because of its lack of availability and inconsistent growth-promoting potential. Human platelet-derived supplements such as platelet lysate (hPL) and platelet-rich plasma have recently been proposed as a superior alternative (Doucet et al. (2005) J Cell Physiol., 205, 228-236; Muller et al. (2006), Cytotherapy., 8, 437-444; Capelli et al. (2007) Bone Marrow Transplant., 40, 785-91; Lange et al. (2007) J Cell Physiol., 213, 18-26; Reinisch et al. (2007) Regen Med., 2, 371-82). While these studies demonstrated considerable growth-promoting properties of pooled human platelet derivatives, their impact on MSC growth is not consistent (Bieback et al. (2008) Transfus Med Hemother., 35, 286-294). Furthermore, the high cost of these hPL formulations can be prohibitive for commercial cell culture.

Accordingly, there remains an unmet need for cost effective methods of supporting both the isolation and rapid expansion of MSC in fetal bovine serum free cell culture.

SUMMARY

The present inventors have found that platelet derived growth factor (PDGF) is required for MSC proliferation in fetal bovine serum free culture conditions. The present inventors have also found that fibroblast growth factor 2 (FGF2) and PDGF synergistically promote MSC proliferation in fetal bovine serum free culture conditions. Surprisingly, this synergistic effect is maintained when FGF2 is present at very low levels. Accordingly, the present inventors have found that they are able to increase in-vitro stem cell proliferation in fetal bovine serum free culture conditions using a specific combination of growth factors. These findings suggest that the methods, culture medium and compositions of the present disclosure may provide a suitable, cost effective replacement for serum that may also be suitable for increasing the efficiency of stem cell culture.

Thus, in one example, the present disclosure relates to a method of promoting stem cell proliferation in-vitro, the method comprising culturing a population of mesenchymal lineage stem cells in a fetal bovine serum free cell culture medium comprising PDGF and FGF2, wherein the level of FGF2 is less than about 6 ng/ml. In another example, the present disclosure relates to a method of promoting mesenchymal lineage precursor cell proliferation in-vitro. In another example, the present disclosure relates to a method of promoting mesenchymal stem cell proliferation in-vitro.

PDGF, FGF2 and any other culture medium components may be provided in a stem cell culture medium or in a composition for addition to a stem cell culture medium for use in the methods of the present disclosure. Thus, in another example, the present disclosure provides a fetal bovine serum free cell culture medium, the cell culture medium comprising:
 a basal medium;
 platelet derived growth factor (PDGF);
 fibroblast growth factor 2 (FGF2);
wherein, the level of FGF2 in the culture medium is less than about 6 ng/ml.

In another example, the level of FGF2 in the culture medium is between about 2 pg/ml and 40 pg/ml. In another example, the level of FGF2 in the culture medium is about 20 pg/ml.

In another example, the PDGF is PDGF-BB or PDGF-AB. In one example, the PDGF is PDGF-BB. In another example, the level of PDGF-BB in the culture medium is between about 3.0 ng/ml and about 120 ng/ml. In another example, level of PDGF-BB in the culture medium is between about 9 ng/ml and about 60 ng/ml. In another example, the level of PDGF-BB in the culture medium is at least about 30 ng/ml.

The present inventors have also found that fibroblast growth factor 2 (FGF2) acts synergistically with other growth factors to promote MSC proliferation. Accordingly, these growth factors can also be used in the methods, cell culture medium and compositions of the present disclosure. In an example, the cell culture medium further comprises epidermal growth factor (EGF). In an example, the level of EGF in the cell culture medium is between about 0.08 ng/ml and about 7 ng/ml. For example, the level of EGF in the cell culture medium is at least about 5 ng/ml. In another example, the level of EGF in the cell culture medium is between about 0.2 ng/ml and about 3.2 ng/ml. In another example, the level of EGF in the cell culture medium is between about 0.4 ng/ml and about 1.6 ng/ml. In another example, the level of EGF is at least about 0.8 ng/ml.

In another example, the medium is for the culture of mesenchymal stem cells. In another example, the medium is for the culture of mesenchymal lineage precursor cells.

In an example, the basal medium is alpha-minimal essential medium or fetal bovine serum free expansion medium such as StemSpan™.

In another example, the cell culture medium maintains the stem cells in an undifferentiated state.

In another example, the present disclosure relates to a composition for addition to a fetal bovine serum free stem cell culture medium, the composition comprising:
  platelet derived growth factor (PDGF);
  fibroblast growth factor 2 (FGF2);
wherein the FGF2 is present in the composition in a sufficient amount to be added to a stem cell culture media at a level less than about 6 ng/ml. In another example, the FGF2 is present in the composition in a sufficient amount to be added to a stem cell culture media at a level between about 5 pg/ml and 40 pg/ml. In another example, the FGF2 is present in the composition in a sufficient amount to be added to a stem cell culture media at a level between about 20 pg/ml.

In another example, the PDGF in the composition is PDGF-BB or PDGF-AB. In one example, the PDGF in the composition is PDGF-BB. In another example, the PDGF-BB is present in the composition in a sufficient amount to be added to a stem cell culture media at a level between about 7.5 ng/ml and about 120 ng/ml. In another example, the PDGF-BB is present in the composition in a sufficient amount to be added to a stem cell culture media at a level between about 15 ng/ml and about 60 ng/ml. In another example, the PDGF-BB is present in the composition in a sufficient amount to be added to a stem cell culture media at a level about at least 30 ng/ml.

In another example, the cell composition further comprises epidermal growth factor (EGF). In one example, the EGF is present in the composition in a sufficient amount to be added to a stem cell culture media at a level between about 0.1 ng/ml and about 7 ng/ml. For example, EGF may be present in the composition in a sufficient amount to be added to a stem cell culture media at a level of about 5 ng/ml. In one example, the EGF is present in the composition in a sufficient amount to be added to a stem cell culture media at a level between about 0.2 ng/ml and about 3.2 ng/ml. In another example, the EGF is present in the composition in a sufficient amount to be added to a stem cell culture media at a level between about 0.4 ng/ml and about 1.6 ng/ml. In another example, the EGF is present in the composition in a sufficient amount to be added to a stem cell culture media at a level about at least 0.8 ng/ml.

In another example, the composition is added to a medium that is suitable for the culture of mesenchymal lineage precursor cells. In another example, the composition is added to a medium that is suitable for the culture of mesenchymal stem cells. In another example, the composition is added to a medium that is suitable for the culture of mesenchymal lineage precursor cells.

In another example, the composition is added to alpha-minimal essential medium or fetal bovine serum free expansion medium such as StemSpan™.

DETAILED DESCRIPTION

General Techniques and Definitions

Figure 1:
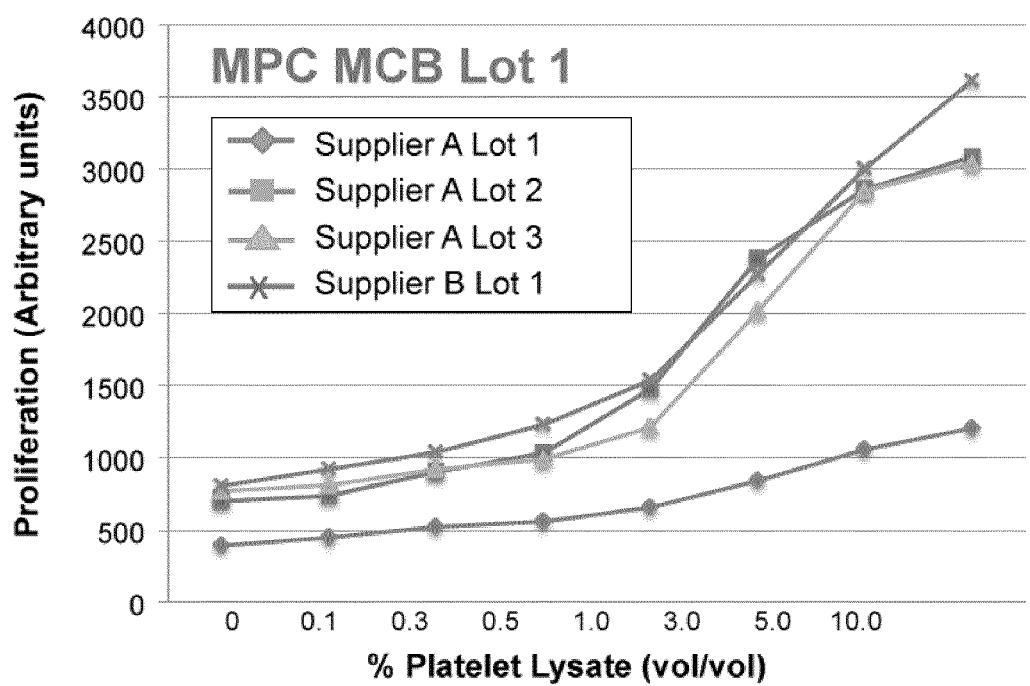
FIG. 1: Effect of platelet lysate percentage on MPC proliferation.

Unless specifically defined otherwise, all technical and scientific terms used herein shall be taken to have the same meaning as commonly understood by one of ordinary skill in the art (e.g., in cell culture, molecular biology, stem cell culture, protein chemistry, and biochemistry).

Unless otherwise indicated, cell culture techniques and assays utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−10%, more preferably +/−5%, of the designated value.

The term "level" is used to define the amount of a particular substance present in the cell culture medium and compositions of the present disclosure. For example, a particular concentration, weight, percentage (e.g. v/v %) or ratio can be used to define the level of a particular substance.

In the context of the present disclosure, the term "sufficient" is used to define an amount that provides a specific concentration when dissolved in a stem cell culture medium. A "sufficient amount" is dictated by the volume of culture medium required. For example, if the required concentration of FGF2 in a stem cell culture medium was about 10 pg/ml and 500 ml of cell culture media was required, a sufficient amount would be about 5 ng.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure, as described herein.

Any example disclosed herein shall be taken to apply mutatis mutandis to any other example unless specifically stated otherwise.

Mesenchymal Lineage Precursor Cells

As used herein, the term "mesenchymal lineage precursor or stem cells" refers to undifferentiated multipotent cells that have the capacity to self renew while maintaining multipotentency and the capacity to differentiate into a number of cell types either of mesenchymal origin, for example, osteoblasts, chondrocytes, adipocytes, stromal cells, fibroblasts and tendons, or non-mesodermal origin, for example, hepatocytes, neural cells and epithelial cells. For the avoidance of doubt, a "mesenchymal lineage precursor cell" refers to a cell which can differentiate into a mesenchymal cell such as bone, cartilage, muscle and fat cells, and fibrous connective tissue.

The term "mesenchymal lineage precursor or stem cells" includes both parent cells and their undifferentiated progeny. The term also includes mesenchymal precursor cells, multipotent stromal cells, mesenchymal stem cells (MSCs), perivascular mesenchymal precursor cells, and their undifferentiated progeny.

Mesenchymal lineage precursor or stem cells can be autologous, xenogenic, syngenic or isogenic. Autologous cells are isolated from the same individual to which they will be reimplanted. Allogeneic cells are isolated from a donor of the same species. Xenogenic cells are isolated from a donor of another species. Syngenic or isogenic cells are isolated from genetically identical organisms, such as twins, clones, or highly inbred research animal models.

Mesenchymal lineage precursor or stem cells reside primarily in the bone marrow, but have also shown to be present in diverse host tissues including, for example, cord blood and umbilical cord, adult peripheral blood, adipose tissue, trabecular bone and dental pulp.

In one example the mesenchymal lineage precursor or stem cells are STRO-1+ mesenchymal precursor cells. As used herein, the phrase "STRO-1+ multipotential cells" shall be taken to mean STRO-1+ and/or TNAP+ progenitor cells capable of forming multipotential cell colonies.

STRO-1+ multipotential cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm. Thus, STRO-1+ multipotential cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues.

Mesenchymal lineage precursor or stem cells can be isolated from host tissues and enriched for by selection of STRO-1+ cells. For example, a bone marrow aspirate from a subject may be further treated with an antibody to STRO-1 or TNAP to enable selection of mesenchymal lineage precursor or stem cells. In one example, the mesenchymal lineage precursor or stem cells can be enriched for by using the STRO-1 antibody described in (Simmons & Torok-Storb, 1991).

The terms "enriched", "enrichment" or variations thereof are used herein to describe a population of cells in which the proportion of one particular cell type or the proportion of a number of particular cell types is increased when compared with an untreated population of the cells (e.g., cells in their native environment). In one example, a population enriched for STRO-1+ cells comprises at least about 0.1% or 0.5% or 1% or 2% or 5% or 10% or 15% or 20% or 25% or 30% or 50% or 75% STRO-1+ cells. In this regard, the term "population of cells enriched for STRO-1+ cells" will be taken to provide explicit support for the term "population of cells comprising X % STRO-1+ cells", wherein X % is a percentage as recited herein. The STRO-1+ cells can, in some examples, form clonogenic colonies, e.g. CFU-F (fibroblasts) or a subset thereof (e.g., 50% or 60% or 70% or 80% or 90% or 95%) can have this activity.

In one example, the population of cells is enriched from a cell preparation comprising STRO-1+ cells in a selectable form. In this regard, the term "selectable form" will be understood to mean that the cells express a marker (e.g., a cell surface marker) permitting selection of the STRO-1+ cells. The marker can be STRO-1, but need not be. For example, cells (e.g., mesenchymal precursor cells) expressing STRO-2 and/or STRO-3 (TNAP) and/or STRO-4 and/or VCAM-1 and/or CD146 and/or 3G5 also express STRO-1 (and can be STRO-1$^{bright}$) Accordingly, an indication that cells are STRO-1+ does not mean that the cells are selected by STRO-1 expression. In one example, the cells are selected based on at least STRO-3 expression, e.g., they are STRO-3+(TNAP+).

Reference to selection of a cell or population thereof does not necessarily require selection from a specific tissue source. As described herein STRO-1+ cells can be selected from or isolated from or enriched from a large variety of sources. That said, in some examples, these terms provide support for selection from any tissue comprising STRO-1+ cells (e.g., mesenchymal precursor cells) or vascularized tissue or tissue comprising pericytes (e.g., STRO-1+ pericytes) or any one or more of the tissues recited herein.

In one example, the mesenchymal lineage precursor or stem cells used in the present disclosure express one or more markers individually or collectively selected from the group consisting of TNAP+, VCAM-1+, THY-1+, STRO-2+, STRO-4+(HSP-90β), CD45+, CD146+, 3G5+ or any combination thereof.

By use of the term "individually" it is meant that the disclosure encompasses the recited markers or groups of markers separately, and that, notwithstanding that individual markers or groups of markers may not be separately listed herein the accompanying claims may define such marker or groups of markers separately and divisibly from each other.

By use of the term "collectively" it is meant that the disclosure encompasses any number or combination of the recited markers or groups of markers, and that, notwithstanding that such numbers or combinations of markers or groups of markers may not be specifically listed herein the accompanying claims may define such combinations or sub-combinations separately and divisibly from any other combination of markers or groups of markers.

In one example, the STRO-1+ cells are STRO-1$^{bright}$ (syn. STRO-1$^{bri}$). In another example, the STRO-1$^{bri}$ cells are preferentially enriched relative to STRO-1$^{dim}$ or STRO-1$^{intermediate}$ cells. In another example, the STRO-1$^{bri}$ cells are additionally one or more of TNAP+, VCAM-1+, THY-1+, STRO-2+, STRO-4+(HSP-90β) and/or CD146+. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the mesenchymal precursor cells are perivascular mesenchymal precursor cells as defined in WO 2004/85630, characterized by the presence of the perivascular marker 3G5.

A cell that is referred to as being "positive" for a given marker may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labelled or is undetectable above background levels, e.g., levels detected using an isotype control antibody.

The term "bright" or "bri" as used herein, refers to a marker on a cell surface that generates a relatively high signal when detectably labelled. Whilst not wishing to be limited by theory, it is proposed that "bright" cells express more of the target marker protein (for example the antigen recognized by STRO-1) than other cells in the sample. For instance, STRO-1$^{bri}$ cells produce a greater fluorescent signal, when labelled with a FITC-conjugated STRO-1 antibody as determined by fluorescence activated cell sorting (FACS) analysis, than non-bright cells (STRO-1$^{dull/dim}$). In one example, "bright" cells constitute at least about 0.1% of the most brightly labelled bone marrow mononuclear cells contained in the starting sample. In other examples, "bright" cells constitute at least about 0.5%, at least about 1%, at least about 1.5%, or at least about 2%, of the most brightly labelled bone marrow mononuclear cells contained in the starting sample. In an example, STRO-1$^{bright}$ cells have 2 log magnitude higher expression of STRO-1 surface expression relative to "background", namely cells that are STRO-1$^-$. By comparison, STRO-1$^{dim}$ and/or STRO-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in one example, the STRO-1+ cells are capable of giving rise to clonogenic CFU-F.

In one example, a significant proportion of the STRO-1+ multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In an aspect of the present disclosure, the presently described mesenchymal lineage precursor or stem cells are MSCs. The MSCs may be a homogeneous composition or may be a mixed cell population enriched in MSCs. Homogeneous MSCs cell compositions may be obtained by culturing adherent marrow or periosteal cells, and the MSCs may be identified by specific cell surface markers which are identified with unique monoclonal antibodies. A method for obtaining a cell population enriched in MSCs is described, for example, in U.S. Pat. No. 5,486,359. Alternative sources for MSCs include, but are not limited to, blood, skin, cord blood, muscle, fat, bone, and perichondrium.

In another example, the mesenchymal lineage precursor or stem cells are CD29+, CD54+, CD73+, CD90+, CD102+, CD105+, CD106+, CD166+, MHC1+ MSCs (e.g. remestemcel-L).

Isolated or enriched mesenchymal lineage precursor or stem cells can be expanded in-vitro by culture. Isolated or enriched mesenchymal lineage precursor or stem cells can be cryopreserved, thawed and subsequently expanded in-vitro by culture.

In one example, isolated or enriched mesenchymal lineage precursor or stem cells are seeded at 50,000 viable cells/cm$^2$ in culture medium (serum free or serum-supplemented), for example, cell culture medium according to the present disclosure, and allowed to adhere to the culture vessel overnight at 37° C., 20% $O_2$. The culture medium is subsequently replaced and/or altered as required and the cells cultured for a further 68 to 72 hours at 37° C., 5% $O_2$.

As will be appreciated by those of skill in the art, cultured mesenchymal lineage precursor or stem cells are phenotypically different to cells in-vivo. For example, in one embodiment they express one or more of the following markers, CD44, NG2, DC146 and CD140b. Cultured mesenchymal lineage precursor or stem cells are also biologically different to cells in-vivo, having a higher rate of proliferation compared to the largely non-cycling (quiescent) cells in-vivo.

Mesenchymal lineage precursor or stem cells cultured using the methods of the present disclosure may also be cryopreserved.

Promoting Cell Proliferation

An aspect of the present disclosure relates to methods of promoting stem cell proliferation in in-vitro cell culture. In the context of the present disclosure, the term "promote" or "promoting" is used to define an increase or acceleration in cell proliferation.

Various methods of identifying increased and/or accelerated cell proliferation are available to those of skill in the art. For example, an increase or acceleration in cell proliferation can be measured based on the number of cells produced over time using, for example, routinely available cell proliferation assays such as MTT assay, Bromodeoxyuridine (BrdU) incorporation assay or real time proliferation assays such as the xCELLigence™ system from Roche.

Accordingly, one of skill in the art could readily determine whether cell proliferation is promoted using the methods of the present disclosure by performing routine proliferation assays known in the art.

In one example of identifying whether cell proliferation is promoted, populations of cells can be cultured in either a cell culture medium according to the present disclosure or an equivalent control medium without PDGF and FGF2 (i.e. the medium of the present disclosure with 0 pg/ml PDGF and FGF2). Cell proliferation in each of the culture mediums can be assessed daily, over a period of time in culture (e.g. seven days) or tracked in real-time. Increased cell numbers or accelerated cell proliferation between day 0 and day 7 indicates that cell proliferation has been promoted.

Promoting Cell Derivation

Stem cells divide asymmetrically to give rise to two distinct daughter cells: one copy of the original stem cell as well as a second daughter cell programmed to differentiate into a non-stem cell fate. For example, pluripotent stem cells can divide to produce one copy of the original stem cell as well as a mesenchymal lineage precursor cell programmed to differentiate into a mesenchymal cell type.

The present disclosure also encompasses methods of promoting stem cell derivation in in-vitro cell culture. For example, the methods of the present disclosure can be used to promote derivation of mesenchymal lineage precursor cell from pluripotent stem cells. In the context of promoting cell derivation, the term "promote" or "promoting" is used to define an increase or acceleration in stem cell derivation.

An aspect of the present disclosure relates to a method of promoting stem cell derivation in-vitro, the method comprising culturing a population of stem cells in a fetal bovine serum free cell culture medium comprising platelet derived growth factor (PDGF) and fibroblast growth factor 2 (FGF2), wherein the level of FGF2 is less than about 6 ng/ml.

For example, the methods of the present disclosure relate to a method of promoting mesenchymal lineage stem cell derivation in-vitro, the method comprising culturing a population of pluripotent stem cells in a fetal bovine serum free cell culture medium comprising platelet derived growth factor (PDGF) and fibroblast growth factor 2 (FGF2), wherein the level of FGF2 is less than about 6 ng/ml.

In another example, the methods of the present disclosure can be used to promote mesenchymal lineage precursor cell derivation from pluripotent stem cells and subsequently promote proliferation of the derived mesenchymal lineage precursor cell population.

Various methods of identifying increased and/or accelerated stem cell derivation are available to those of skill in the art. For example, increased or accelerated mesenchymal lineage precursor cell derivation can be measured based on the number of mesenchymal lineage precursor cells produced from pluripotent stem cells over time. Mesenchymal lineage precursor cells are characterized by specific surface markers, the expression of which facilitates their isolation and purification by immunoselection. Examples of these markers include STRO-1+, TNAP+, VCAM-1+, THY-1+, STRO-2+, STRO-4+(HSP-90β), CD146+, 3G5+ or combinations thereof. Accordingly, one of skill in the art could use immunoselection to purify and count the mesenchymal lineage precursor cells in a population. Cell numbers could be used to identify the number of mesenchymal lineage precursor cells produced over time and determine whether mesenchymal lineage precursor cell derivation is increased or accelerated.

In another example of identifying whether cell derivation is promoted, populations of pluripotent stem cells can be cultured in either a cell culture medium according to the present disclosure or an equivalent control medium without PDGF and FGF2 (i.e. the medium of the present disclosure with 0 pg/ml PDGF and FGF2). Derivation of mesenchymal lineage precursor cells in each of the culture mediums can be assessed daily or over a period of time in culture (e.g. seven days) by immunoselecting mesenchymal lineage precursor cells from cell culture and determining the number of cells produced. Increased mesenchymal lineage precursor cell numbers between day 0 and day 7 relative to control cell numbers indicates that cell derivation was promoted.

Cell Culture Medium

The present disclosure provides fetal bovine serum free stem cell culture medium comprising growth factors that promote MSC proliferation. In an embodiment, the present disclosure relates to a fetal bovine serum free stem cell culture medium, the cell culture medium comprising:
 a basal medium;
 platelet derived growth factor (PDGF);
 fibroblast growth factor 2 (FGF2).

The term "medium" or "media" as used in the context of the present disclosure, includes the components of the environment surrounding the cells. The media contributes to and/or provides the conditions suitable to allow cells to grow. Media may be solid, liquid, gaseous or a mixture of phases and materials. Media can include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells.

The culture media of the present disclosure can be prepared by using a basal culture medium. In the context of the present disclosure, "basal culture medium" refers to an unsupplemented medium which is suitable for exposure to cells, for example MSC. Basal culture medium includes, for example, Eagles minimal essential (MEM) culture media, alpha modified MEM culture media, StemSpan™ and mixed culture media thereof, and is not particularly restricted providing it can be used for culturing of stem cells.

Further, the cell culture medium of the present disclosure can contain any components such as fatty acids or lipids, vitamins, cytokines, antioxidants, buffering agents, inorganic salts and the like.

The cell culture media used in the present disclosure contains all essential amino acids and may also contain non-essential amino acids. In general, amino acids are classified into essential amino acids (Thr, Met, Val, Leu, Ile, Phe, Trp, Lys, His) and non-essential amino acids (Gly, Ala, Ser, Cys, Gln, Asn, Asp, Tyr, Arg, Pro).

Those of skill in the art will appreciate that for optimal results, the basal medium must be appropriate for the cell line of interest with key nutrients available at adequate levels to enhance cell proliferation. For example, it may be necessary to increase the level of glucose (or other energy source) in the basal medium, or to add glucose (or other energy source) during the course of culture, if this energy source is found to be depleted and to thus limit cell proliferation.

In an example, the cell culture medium of the present disclosure contains human derived additives. For example, human serum and human platelet cell lysate can be added to the cell culture media used in the methods of the present disclosure.

In an example, the cell culture medium of the present disclosure contains only human derived additives. Thus, in an example, the cell culture media is xeno-free.

Ascorbic Acid

Ascorbic acid is an essential supplement for the growth and differentiation of various kinds of cells in culture. It is now understood that particular ascorbic acid derivatives are "short acting" because they are not stable in solution, especially under the normal cell culture conditions of neutral pH and 37° C. These short acting derivatives rapidly oxidise into oxalic acid or threonic acid. In culture media (pH 7) at 37° C., oxidation decreases the level of these short acting ascorbic acid derivatives by approximately 80-90% in 24 hours. Accordingly, short acting ascorbic acid derivatives have been replaced with more stable "long acting" ascorbic acid derivatives in conventional cell culture of various cell types.

In the context of the present disclosure the term "short acting" encompasses ascorbic acid derivatives that are oxidised by approximately 80-90% following 24 hours of cell culture under culture conditions of neutral pH and 37° C. In one example, the short acting L-ascorbic acid derivative is a L-ascorbic acid salt. For example, in the context of the present disclosure, L-ascorbic acid sodium salt is a "short acting" ascorbic acid derivative.

In contrast, the term "long acting" encompasses ascorbic acid derivatives that are not oxidised by approximately 80-90% following 24 hours of cell culture under culture conditions of neutral pH and 37° C. In one example, in the context of the present disclosure, L-ascorbic acid-2-phosphate is a "long acting" ascorbic acid derivative. Other examples of long acting ascorbic acid derivatives include Tetrahexyldecyl Ascorbate Magnesium Ascorbyl Phosphate and 2-O-α-D-Glucopyranosyl-L-ascorbic acid. The cell culture medium of the present disclosure can contain short acting ascorbic acid derivatives, long acting ascorbic acid derivatives or mixtures thereof.

Serum

Conventionally, stem cells are maintained in cell culture using media supplemented with at least about 10-15% v/v serum, generally fetal bovine serum (FBS), also known as fetal calf serum (FCS). The cell culture medium of the present disclosure is a fetal bovine serum-free cell culture medium. Thus, in an embodiment, the cell culture media is supplemented with a non-fetal serum. For example, the culture media may be supplemented with a neo-natal or adult serum In another embodiment, the cell culture medium is supplemented with human serum. In an example, the cell culture media can be supplemented with human non-fetal serum. For example, the cell culture media can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v human non-fetal serum.

In another example, the cell culture medium can be supplemented with human neo-natal serum. For example, the cell culture medium can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9% v/v human neo-natal serum. In an example, the human neo-natal serum is obtained from umbilical cord blood "cord blood".

In another example, the cell culture medium can be supplemented with human adult serum. For example, the culture media can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v human adult serum.

In an example, the human adult serum is human AB serum. For example, the cell culture medium can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9% v/v human AB serum. In an example, the cell culture medium is supplemented with at least about 3% human AB serum.

The cell culture medium of the present disclosure may also contain known serum replacements. The serum replacement can be, for example, albumin (for example, lipid-rich albumin), transferrin, fatty acid, insulin, collagen precursor, trace element, 2-mercaptoethanol or 3'-thiol glycerol, platelet lysate, platelet-rich plasma, or those appropriately containing serum equivalents. Such a serum replacement can be prepared, for example, by a method described in International Publication WO 93/30679, and commercially available products can also be used.

Mitogenic Factors

The present inventors have found that PDGF and FGF2 synergistically promote stem cell proliferation in in-vitro fetal bovine serum free cell culture.

PDGF is a regulator of cell growth and division which binds to platelet derived growth factor receptors (PDGFR). In chemical terms, PDGF is a dimeric glycoprotein composed of two A (-AA) or two B (-BB) chains or a combination of the two (-AB). PDGF-AB has been shown to bind PDGF alpha and beta receptor subunits to form PDGF alpha beta and alpha alpha receptor dimers. In the context of the present disclosure PDGF encompasses PDGF-BB and PDGF-AB.

Basic fibroblast growth factor (FGF2) also known as BFGF, FGFB, HBGF-2 is a member of the fibroblast growth factor (FGF) family. FGF2 is also a regulator of cell growth and division. Both PDGF and FGF2 can be classified as mitogens in that they encourage a cell to commence cell division.

In an example, the method of the present disclosure comprises culturing a population of stem cells in a fetal bovine serum free cell culture medium comprising platelet derived growth factor (PDGF) and fibroblast growth factor 2 (FGF2), wherein the level of FGF2 is less than about 6 ng/ml. For example, the FGF2 level may be less than about 5 ng/ml, less than about 4 ng/ml, less than about 3 ng/ml, less than about 2 ng/ml, less than about 1 ng/ml. In other examples, the FGF2 level is less than about 0.9 ng/ml, less than about 0.8 ng/ml, less than about 0.7 ng/ml, less than about 0.6 ng/ml, less than about 0.5 ng/ml, less than about 0.4 ng/ml, less than about 0.3 ng/ml, less than about 0.2 ng/ml.

In another example, the level of FGF2 is between about 1 pg/ml and 100 pg/ml. In another example, the level of FGF2 is between about 5 pg/ml and 80 pg/ml. In another example, the level of FGF2 is between about 10 pg/ml and 40 pg/ml. In another example, the level of FGF2 is at least about 10 pg/ml. In another example, the level of FGF2 is at least about 11 pg/ml. In another example, the level of FGF2 is at least about 12 pg/ml. In another example, the level of FGF2 is at least about 13 pg/ml. In another example, the level of FGF2 is at least about 14 pg/ml. In another example, the level of FGF2 is at least about 15 pg/ml. In another example, the level of FGF2 is at least about 16 pg/ml. In another example, the level of FGF2 is at least about 17 pg/ml. In another example, the level of FGF2 is at least about 18 pg/ml. In another example, the level of FGF2 is at least about 19 pg/ml. In another example, the level of FGF2 is at least about 20 pg/ml. In another example, the level of FGF2 is at least about 21 pg/ml. In another example, the level of FGF2 is at least about 22 pg/ml. In another example, the level of FGF2 is at least about 23 pg/ml. In another example, the level of FGF2 is at least about 24 pg/ml. In another example, the level of FGF2 is at least about 25 pg/ml. In another example, the level of FGF2 is at least about 26 pg/ml. In another example, the level of FGF2 is at least about 27 pg/ml. In another example, the level of FGF2 is at least about 28 pg/ml. In another example, the level of FGF2 is at least about 29 pg/ml. In another example, the level of FGF2 is at least about 30 pg/ml.

In an example, the PDGF is PDGF-BB. In an example, the level of PDGF-BB is between about 1 ng/ml and 150 ng/ml. In another example, the level of PDGF-BB is between about 7.5 ng/ml and 120 ng/ml. In another example, the level of PDGF-BB is between about 15 ng/ml and 60 ng/ml. In another example, the level of PDGF-BB is at least about 10 ng/ml. In another example, the level of PDGF-BB is at least about 15 ng/ml. In another example, the level of PDGF-BB is at least about 20 ng/ml. In another example, the level of PDGF-BB is at least about 21 ng/ml. In another example, the level of PDGF-BB is at least about 22 ng/ml. In another example, the level of PDGF-BB is at least about 23 ng/ml. In another example, the level of PDGF-BB is at least about 24 ng/ml. In another example, the level of PDGF-BB is at least about 25 ng/ml. In another example, the level of PDGF-BB is at least about 26 ng/ml. In another example, the level of PDGF-BB is at least about 27 ng/ml. In another example, the level of PDGF-BB is at least about 28 ng/ml. In another example, the level of PDGF-BB is at least about 29 ng/ml. In another example, the level of PDGF-BB is at least about 30 ng/ml. In another example, the level of PDGF-BB is at least about 31 ng/ml. In another example, the level of PDGF-BB is at least about 32 ng/ml. In another example, the level of PDGF-BB is at least about 33 ng/ml. In another example, the level of PDGF-BB is at least about 34 ng/ml. In another example, the level of PDGF-BB is at least about 35 ng/ml. In another example, the level of PDGF-BB is at least about 36 ng/ml. In another example, the level of PDGF-BB is at least about 37 ng/ml. In another example, the level of PDGF-BB is at least about 38 ng/ml. In another example, the level of PDGF-BB is at least about 39 ng/ml. In another example, the level of PDGF-BB is at least about 40 ng/ml.

In another example, the PDGF is PDGF-AB. In an example, the level of PDGF-AB is between about 1 ng/ml and 150 ng/ml. In another example, the level of PDGF-AB is between about 7.5 ng/ml and 120 ng/ml. In another example, the level of PDGF-AB is between about 15 ng/ml and 60 ng/ml. In another example, the level of PDGF-AB is at least about 10 ng/ml. In another example, the level of PDGF-AB is at least about 15 ng/ml. In another example, the level of PDGF-AB is at least about 20 ng/ml. In another example, the level of PDGF-AB is at least about 21 ng/ml. In another example, the level of PDGF-AB is at least about 22 ng/ml. In another example, the level of PDGF-AB is at least about 23 ng/ml. In another example, the level of PDGF-AB is at least about 24 ng/ml. In another example, the level of PDGF-AB is at least about 25 ng/ml. In another example, the level of PDGF-AB is at least about 26 ng/ml. In another example, the level of PDGF-AB is at least about 27 ng/ml. In another example, the level of PDGF-AB is at least about 28 ng/ml. In another example, the level of PDGF-AB is at least about 29 ng/ml. In another example, the level of PDGF-AB is at least about 30 ng/ml. In another example, the level of PDGF-AB is at least about 31 ng/ml. In another example, the level of PDGF-AB is at least about 32 ng/ml. In another example, the level of PDGF-AB is at least about 33 ng/ml. In another example, the level of PDGF-AB is at least about 34 ng/ml. In another example, the level of PDGF-AB is at least about 35 ng/ml. In another example, the level of PDGF-AB is at least about 36 ng/ml. In another example, the level of PDGF-AB is at least about 37 ng/ml. In another example, the level of PDGF-AB is at least about 38 ng/ml. In another example, the level of PDGF-AB is at least about 39 ng/ml. In another example, the level of PDGF-AB is at least about 40 ng/ml.

The present inventors have also found that other factors can be added to the cell culture medium of the present disclosure to increase cell proliferation. In an example, the method of the present disclosure comprises culturing a population of stem cells in a fetal bovine serum free cell culture medium further comprising EGF. EGF is a growth factor that stimulates cell proliferation by binding to its receptor EGFR. In an example, the method of the present disclosure comprises culturing a population of stem cells in a fetal bovine serum free cell culture medium further comprising EGF. In an example, the level of EGF is between about 0.1 and 7 ng/ml. For example, the level of EGF can be at least about 5 ng/ml.

In another example, the level of EGF is between about 0.2 ng/ml and 3.2 ng/ml. In another example, the level of EGF is between about 0.4 ng/ml and 1.6 ng/ml. In another example, the level of EGF is between about 0.2 ng/ml. In another example, the level of EGF is at least about 0.3 ng/ml. In another example, the level of EGF is at least about 0.4 ng/ml. In another example, the level of EGF is at least about 0.5 ng/ml. In another example, the level of EGF is at least about 0.6 ng/ml. In another example, the level of EGF is at least about 0.7 ng/ml. In another example, the level of EGF is at least about 0.8 ng/ml. In another example, the level of EGF is at least about 0.9 ng/ml. In another example, the level of EGF is at least about 1.0 ng/ml. In another example, the level of EGF is at least about 1.1 ng/ml. In another example, the level of EGF is at least about 1.2 ng/ml. In another example, the level of EGF is at least about 1.3 ng/ml. In another example, the level of EGF is at least about 1.4 ng/ml.

In an example, the level of PDGF-BB is at least about 3.2 ng/ml, the level of EGF is at least about 0.8 ng/ml and the level of FGF2 is at least about 0.002 ng/ml. In another example, the level of PDGF-BB is at least about 9.6 ng/ml, the level of EGF is at least about 0.24 ng/ml and the level of FGF2 is at least about 0.006 ng/ml. In another example, the level of PDGF-BB is at least about 16 ng/ml, the level of EGF is at least about 0.40 ng/ml and the level of FGF2 is at least about 0.01 ng/ml. In another example, the level of PDGF-BB is at least about 32 ng/ml, the level of EGF is at least about 0.80 ng/ml and the level of FGF2 is at least about 0.01 ng/ml.

The present disclosure also encompasses cell culture medium comprising PDGF and FGF2, wherein the level of FGF2 is less than about 6 ng/ml. For example, the FGF2 level may be less than about 5 ng/ml, less than about 4 ng/ml, less than about 3 ng/ml, less than about 2 ng/ml, less than about 1 ng/ml. In other examples, the FGF2 level is less than about 0.9 ng/ml, less than about 0.8 ng/ml, less than about 0.7 ng/ml, less than about 0.6 ng/ml, less than about 0.5 ng/ml, less than about 0.4 ng/ml, less than about 0.3 ng/ml, less than about 0.2 ng/ml.

In an example, the cell culture medium contains between about 1 pg/ml and 100 pg/ml of FGF2. In another example, the cell culture medium contains between about 5 pg/ml and 80 pg/ml of FGF2. In another example, the cell culture medium contains between about 10 pg/ml and 40 pg/ml of FGF2. For example, the cell culture medium may contain at least about 10 pg/ml of FGF2. For example, the cell culture medium may contain at least about 11 pg/ml of FGF2. For example, the cell culture medium may contain at least about 12 pg/ml of FGF2. For example, the cell culture medium may contain at least about 13 pg/ml of FGF2. For example, the cell culture medium may contain at least about 14 pg/ml of FGF2. For example, the cell culture medium may contain at least about 15 pg/ml of FGF2. For example, the cell culture medium may contain at least about 16 pg/ml of FGF2. For example, the cell culture medium may contain at least about 17 pg/ml of FGF2. For example, the cell culture medium may contain at least about 18 pg/ml of FGF2. For example, the cell culture medium may contain at least about 19 pg/ml of FGF2. For example, the cell culture medium may contain at least about 20 pg/ml of FGF2. For example, the cell culture medium may contain at least about 21 pg/ml of FGF2. For example, the cell culture medium may contain at least about 22 pg/ml of FGF2. For example, the cell culture medium may contain at least about 23 pg/ml of FGF2. For example, the cell culture medium may contain at least about 24 pg/ml of FGF2. For example, the cell culture medium may contain at least about 25 pg/ml of FGF2. For example, the cell culture medium may contain at least about 26 pg/ml of FGF2. For example, the cell culture medium may contain at least about 27 pg/ml of FGF2. For example, the cell culture medium may contain at least about 28 pg/ml of FGF2. For example, the cell culture medium may contain at least about 29 pg/ml of FGF2. For example, the cell culture medium may contain at least about 30 pg/ml of FGF2.

In an embodiment the cell culture medium of the present disclosure is supplemented with PDGF-BB. For example, the cell culture medium may contain between about 1 ng/ml and 150 ng/ml of PDGF-BB. In another example, the cell culture medium may contain between about 7.5 ng/ml and 120 ng/ml of PDGF-BB. In another example, the cell culture medium may contain between about 15 ng/ml and 60 ng/ml of PDGF-BB. For example, the cell culture medium may contain at least about 10 ng/ml of PDGF-BB. For example, the cell culture medium may contain at least about 15 ng/ml of PDGF-BB. For example, the cell culture medium may contain at least about 20 ng/ml of PDGF-BB. For example, the cell culture medium may contain at least about 21 ng/ml of PDGF-BB. For example, the cell culture medium may contain at least about 22 ng/ml of PDGF-BB. For example, the cell culture medium may contain at least about 23 ng/ml of PDGF-BB. For example, the cell culture medium may contain at least about 24 ng/ml of PDGF-BB. For example, the cell culture medium may contain at least about 25 ng/ml of PDGF-BB. For example, the cell culture medium may contain at least about 26 ng/ml of PDGF-BB. For example, the cell culture medium may contain at least about 27 ng/ml of PDGF-BB. For example, the cell culture medium may contain at least about 28 ng/ml of PDGF-BB. For example, the cell culture medium may contain at least about 29 ng/ml of PDGF-BB. For example, the cell culture medium may contain at least about 30 ng/ml of PDGF-BB. For example, the cell culture medium may contain at least about 31 ng/ml of PDGF-BB. For example, the cell culture medium may contain at least about 32 ng/ml of PDGF-BB. For example, the cell culture medium may contain at least about 33 ng/ml of PDGF-BB. For example, the cell culture medium may contain at least at least about 34 ng/ml of PDGF-BB. For example, the cell culture medium may contain at least about 35 ng/ml of PDGF-BB. For example, the cell culture medium may contain at least about 36 ng/ml of PDGF-BB. For example, the cell culture medium may contain at least about 37 ng/ml of PDGF-BB. For example, the cell culture medium may contain at least about 38 ng/ml of PDGF-BB. For example, the cell culture medium may contain at least about 39 ng/ml of PDGF-BB. For example, the cell culture medium may contain at least about 40 ng/ml of PDGF-BB.

In an embodiment the cell culture medium of the present disclosure is supplemented with PDGF-AB. For example, the cell culture medium may contain between about 1 ng/ml and 150 ng/ml of PDGF-AB. In another example, the cell culture medium may contain between about 7.5 ng/ml and 120 ng/ml of PDGF-AB. In another example, the cell culture medium may contain between about 15 ng/ml and 60 ng/ml of PDGF-AB. For example, the cell culture medium may contain at least about 10 ng/ml of PDGF-AB. For example, the cell culture medium may contain at least about 15 ng/ml of PDGF-AB. For example, the cell culture medium may contain at least about 20 ng/ml of PDGF-AB. For example, the cell culture medium may contain at least about 21 ng/ml of PDGF-AB. For example, the cell culture medium may contain at least about 22 ng/ml of PDGF-AB. For example, the cell culture medium may contain at least about 23 ng/ml of PDGF-AB. For example, the cell culture medium may contain at least about 24 ng/ml of PDGF-AB. For example, the cell culture medium may contain at least about 25 ng/ml of PDGF-AB. For example, the cell culture medium may contain at least about 26 ng/ml of PDGF-AB. For example, the cell culture medium may contain at least about 27 ng/ml of PDGF-AB. For example, the cell culture medium may contain at least about 28 ng/ml of PDGF-AB. For example, the cell culture medium may contain at least about 29 ng/ml of PDGF-AB. For example, the cell culture medium may contain at least about 30 ng/ml of PDGF-AB. For example, the cell culture medium may contain at least about 31 ng/ml of PDGF-AB. For example, the cell culture medium may contain at least about 32 ng/ml of PDGF-AB. For example, the cell culture medium may contain at least about 33 ng/ml of PDGF-AB. For example, the cell culture medium may contain at least about 34 ng/ml of PDGF-AB. For example, the cell culture medium may contain at least about 35 ng/ml of PDGF-AB. For example, the cell culture medium may contain at least about 36 ng/ml of PDGF-AB. For example, the cell culture medium may contain at least about 37 ng/ml of PDGF-AB. For example, the cell culture medium may contain at least about 38 ng/ml of PDGF-AB. For example, the cell culture medium may contain at least about 39 ng/ml of PDGF-AB. For example, the cell culture medium may contain at least about 40 ng/ml of PDGF-AB.

In an embodiment, the cell culture medium of the present disclosure can also be supplemented with EGF. For example, the cell culture medium may contain between about 0.1 ng/ml and 7 ng/ml of EGF. For example, the level of EGF can be at least about 5 ng/ml.

In another example, the cell culture medium may contain between about 0.2 ng/ml and 3.2 ng/ml of EGF. In another example, the cell culture medium may contain between about 0.4 ng/ml and 1.6 ng/ml of EGF. For example, the cell culture medium may contain at least about 0.2 ng/ml of EGF. For example, the cell culture medium may contain at least about 0.3 ng/ml of EGF. For example, the cell culture medium may contain at least about 0.4 ng/ml of EGF. For example, the cell culture medium may contain at least about 0.5 ng/ml of EGF. For example, the cell culture medium may contain at least about 0.6 ng/ml of EGF. For example, the cell culture medium may contain at least about 0.7 ng/ml of EGF. For example, the cell culture medium may contain at least about 0.8 ng/ml of EGF. For example, the cell culture medium may contain at least about 0.9 ng/ml of EGF. For example, the cell culture medium may contain at least about 1.0 ng/ml of EGF. For example, the cell culture medium may contain at least about 1.1 ng/ml of EGF. For example, the cell culture medium may contain at least about 1.2 ng/ml of EGF. For example, the cell culture medium may contain at least about 1.3 ng/ml of EGF. For example, the cell culture medium may contain at least about 1.4 ng/ml of EGF.

For example, the cell culture medium may contain at least about 3.2 ng/ml PDGF-BB, at least about 0.08 ng/ml EGF and at least about 0.002 ng/ml FGF2. In another example, the cell culture medium may contain at least about 9.6 ng/ml PDGF-BB, at least about 0.24 ng/ml EGF and at least about 0.006 ng/ml FGF2. In another example, the cell culture medium may contain at least about 16 ng/ml PDGF-BB, at least about 0.40 ng/ml EGF and at least about 0.01 ng/ml FGF2. In another example, the cell culture medium may contain at least about 32 ng/ml PDGF-BB, at least about 0.80 ng/ml EGF and at least about 0.02 ng/ml FGF2.

Other factors can be added to the cell culture medium of the present disclosure to increase cell proliferation. For example, the cell culture media can be supplemented with one or more stimulatory factors selected from the group consisting of epidermal growth factor (EGF), 1α,25-dihydroxyvitamin D3 (1,25D), tumor necrosis factor α (TNF-α), interleukin-1β (IL-1β) and stromal derived factor 1α (SDF-1α). In another embodiment, cells may also be cultured in the presence of at least one cytokine in an amount adequate to support growth of the cells. In another embodiment, cells can be cultured in the presence of heparin or a derivative thereof. For example, the cell culture medium may contain about 50 ng/ml of heparin. In other examples, the cell culture medium contains about 60 ng/ml of heparin, about 70 ng/ml of heparin, about 80 ng/ml of heparin, about 90 ng/ml of heparin, about 100 ng/ml of heparin, about 110 ng/ml of heparin, about 110 ng/ml of heparin, about 120 ng/ml of heparin, about 130 ng/ml of heparin, about 140 ng/ml of heparin, about 150 ng/ml of heparin or a derivative thereof. In an example, the heparin derivative is a sulphate). Various forms of heparin sulphate are known in the art and include heparin sulphate 2 (HS2). HS2 can be derived from various sources including for example, the liver of male and/or female mammals. Thus, an exemplary heparin sulphate includes male liver heparin sulphate (MML HS) and female liver heparin sulphate (FML HS).

In another example, the methods and cell culture medium of the present disclosure promote stem cell proliferation while maintaining stem cells in an undifferentiated state. Stem cells are considered to be undifferentiated when they have not committed to a specific differentiation lineage. As discussed above, stem cells display morphological characteristics that distinguish them from differentiated cells. Furthermore, undifferentiated stem cells express genes that may be used as markers to detect differentiation status. The polypeptide products may also be used as markers to detect differentiation status. Accordingly, one of skill in the art could readily determine whether the methods of the present disclosure maintain stem cells in an undifferentiated state using routine morphological, genetic and/or proteomic analysis.

Compositions/Kits

The cell culture medium of the present disclosure can be provided as a complete medium wherein the basal medium and the growth factors have been mixed together prior to cell culture. Alternatively, the cell culture medium components can be provided separately and mixed with a suitable basal medium prior to or during cell culture. Accordingly, in an embodiment, the present disclosure provides a serum replacement composition for addition to a stem cell culture medium, the composition comprising:

platelet derived growth factor (PDGF);

fibroblast growth factor 2 (FGF2);

wherein, when the composition is added to a stem cell culture medium and a stem cell population is cultured in the cell culture medium, the level of FGF2 in the culture medium is less than about 6 ng/ml. In other examples, when the composition is added to a stem cell culture medium and a stem cell population is cultured in the cell culture medium the FGF2 level may be less than about 5 ng/ml, less than about 4 ng/ml, less than about 3 ng/ml, less than about 2 ng/ml, less than about 1 ng/ml. In other examples, the FGF2 level is less than about 0.9 ng/ml, less than about 0.8 ng/ml, less than about 0.7 ng/ml, less than about 0.6 ng/ml, less than about 0.5 ng/ml, less than about 0.4 ng/ml, less than about 0.3 ng/ml, less than about 0.2 ng/ml.

In an example, FGF2 is present in a sufficient amount to be added to a stem cell culture media at a level between about 1 pg/ml and 100 pg/ml. In another example, FGF2 is present in a sufficient amount to be added to a stem cell culture media at a level between about 5 pg/ml and 80 pg/ml. In another example, FGF2 is present in a sufficient amount to be added to a stem cell culture media at a level between about 10 pg/ml and 40 pg/ml. For example, FGF2 may be present in a sufficient amount to be added to a stem cell culture media at least at about 10 pg/ml. For example, FGF2 may be present in a sufficient amount to be added to a stem cell culture media at least at about 11 pg/ml. For example, FGF2 may be present in a sufficient amount to be added to a stem cell culture media at least at about 12 pg/ml. For example, FGF2 may be present in a sufficient amount to be added to a stem cell culture media at about least at 13 pg/ml. For example, FGF2 may be present in a sufficient amount to be added to a stem cell culture media at least at about 14 pg/ml. For example, FGF2 may be present in a sufficient amount to be added to a stem cell culture media at least at about 15 pg/ml. For example, FGF2 may be present in a sufficient amount to be added to a stem cell culture media at least at about 16 pg/ml. For example, FGF2 may be present in a sufficient amount to be added to a stem cell culture media at least at about 17 pg/ml. For example, FGF2 may be present in a sufficient amount to be added to a stem cell culture media at least at about 18 pg/ml. For example, FGF2 may be present in a sufficient amount to be added to a stem cell culture media at about 19 pg/ml. For example, FGF2 may be present in a sufficient amount to be added to a stem cell culture media at least at about 20 pg/ml. For example, FGF2 may be present in a sufficient amount to be added to a stem cell culture media at least at about 21 pg/ml. For example, FGF2 may be present in a sufficient amount to be added to a stem cell culture media at least at about 22 pg/ml. For example, FGF2 may be present in a sufficient amount to be added to a stem cell culture media at least at about 23 pg/ml. For example, FGF2 may be present in a sufficient amount to be added to a stem cell culture media at least at about 24 pg/ml. For example, FGF2 may be present in a sufficient amount to be added to a stem cell culture media at least at about 25 pg/ml. For example, FGF2 may be present in a sufficient amount to be added to a stem cell culture media at least at about 26 pg/ml. For example, FGF2 may be present in a sufficient amount to be added to a stem cell culture media at least at about 27 pg/ml. For example, FGF2 may be present in a sufficient amount to be added to a stem cell culture media at least at about 28 pg/ml. For example, FGF2 may be present in a sufficient amount to be added to a stem cell culture media at least at about 29 pg/ml. For example, FGF2 may be present in a sufficient amount to be added to a stem cell culture media at least at about 30 pg/ml.

In an embodiment PDGF-BB is present in the composition of the present disclosure. For example, PDGF-BB may be present in a sufficient amount to be added to a stem cell culture media at about 1 ng/ml and 150 ng/ml. In another example, PDGF-BB may be present in a sufficient amount to be added to a stem cell culture media at about 7.5 ng/ml and 120 ng/ml. In another example, PDGF-BB may be present in a sufficient amount to be added to a stem cell culture media at about 15 ng/ml and 60 ng/ml. For example, PDGF-BB may be present in a sufficient amount to be added to a stem cell culture media at least at about 10 ng/ml. For example, PDGF-BB may be present in a sufficient amount to be added to a stem cell culture media at least at about 15 ng/ml. For example, PDGF-BB may be present in a sufficient amount to be added to a stem cell culture media at least at about 20 ng/ml. For example, PDGF-BB may be present in a sufficient amount to be added to a stem cell culture media at least at about 21 ng/ml. For example, PDGF-BB may be present in a sufficient amount to be added to a stem cell culture media at least at about 22 ng/ml. For example, PDGF-BB may be present in a sufficient amount to be added to a stem cell culture media at least at about 23 ng/ml. For example, PDGF-BB may be present in a sufficient amount to be added to a stem cell culture media at least at about 24 ng/ml. For example, PDGF-BB may be present in a sufficient amount to be added to a stem cell culture media at least at about 25 ng/ml. For example, PDGF-BB may be present in a sufficient amount to be added to a stem cell culture media at least at about 26 ng/ml. For example, PDGF-BB may be present in a sufficient amount to be added to a stem cell culture media at least at about 27 ng/ml. For example, PDGF-BB may be present in a sufficient amount to be added to a stem cell culture media at least at about 28 ng/ml. For example, PDGF-BB may be present in a sufficient amount to be added to a stem cell culture media at least at about 29 ng/ml. For example, PDGF-BB may be present in a sufficient amount to be added to a stem cell culture media at least at about 30 ng/ml. For example, PDGF-BB may be present in a sufficient amount to be added to a stem cell culture media at least at about 31 ng/ml. For example, PDGF-BB may be present in a sufficient amount to be added to a stem cell culture media at least at about 32 ng/ml. For example, PDGF-BB may be present in a sufficient amount to be added to a stem cell culture media at least at about 33 ng/ml. For example, PDGF-BB may be present in a sufficient amount to be added to a stem cell culture media at least at about 34 ng/ml. For example, PDGF-BB may be present in a sufficient amount to be added to a stem cell culture media at least at about 35 ng/ml. For example, PDGF-BB may be present in a sufficient amount to be added to a stem cell culture media at least at about 36 ng/ml. For example, PDGF-BB may be present in a sufficient amount to be added to a stem cell culture media at least at about 37 ng/ml. For example, PDGF-BB may be present in a sufficient amount to be added to a stem cell culture media at least at about 38 ng/ml. For example, PDGF-BB may be present in a sufficient amount to be added to a stem cell culture media at least at about 39 ng/ml. For example, PDGF-BB may be present in a sufficient amount to be added to a stem cell culture media at least at about 40 ng/ml.

In an embodiment the composition of the present disclosure comprises PDGF-AB. For example, PDGF-AB may be present in a sufficient amount to be added to a stem cell culture media at about 1 ng/ml and 150 ng/ml. In another example, PDGF-AB may be present in a sufficient amount to be added to a stem cell culture media at about 7.5 ng/ml and 120 ng/ml. In another example, PDGF-AB may be present in a sufficient amount to be added to a stem cell culture media at about 15 ng/ml and 60 ng/ml. For example, PDGF-AB may be present in a sufficient amount to be added to a stem cell culture media at least at about 10 ng/ml. For example, PDGF-AB may be present in a sufficient amount to be added to a stem cell culture media at least at about 15 ng/ml. For example, PDGF-AB may be present in a sufficient amount to be added to a stem cell culture media at least at about 20 ng/ml. For example, PDGF-AB may be present in a sufficient amount to be added to a stem cell culture media at least at about 21 ng/ml. For example, PDGF-AB may be present in a sufficient amount to be added to a stem cell culture media at least at about 22 ng/ml. For example, PDGF-AB may be present in a sufficient amount to be added to a stem cell culture media at least at about 23 ng/ml. For example, PDGF-AB may be present in a sufficient amount to be added to a stem cell culture media at least at about 24 ng/ml. For example, PDGF-AB may be present in a sufficient amount to be added to a stem cell culture media at least at about 25 ng/ml. For example, PDGF-AB may be present in a sufficient amount to be added to a stem cell culture media at least at about 26 ng/ml. For example, PDGF-AB may be present in a sufficient amount to be added to a stem cell culture media at least at about 27 ng/ml. For example, PDGF-AB may be present in a sufficient amount to be added to a stem cell culture media at least at about 28 ng/ml. For example, PDGF-AB may be present in a sufficient amount to be added to a stem cell culture media at least at about 29 ng/ml. For example, PDGF-AB may be present in a sufficient amount to be added to a stem cell culture media at least at about 30 ng/ml. For example, PDGF-AB may be present in a sufficient amount to be added to a stem cell culture media at least at about 31 ng/ml. For example, PDGF-AB may be present in a sufficient amount to be added to a stem cell culture media at least at about 32 ng/ml. For example, PDGF-AB may be present in a sufficient amount to be added to a stem cell culture media at least at about 33 ng/ml. For example, PDGF-AB may be present in a sufficient amount to be added to a stem cell culture media at least at about 34 ng/ml. For example, PDGF-AB may be present in a sufficient amount to be added to a stem cell culture media at least at about 35 ng/ml. For example, PDGF-AB may be present in a sufficient amount to be added to a stem cell culture media at least at about 36 ng/ml. For example, PDGF-AB may be present in a sufficient amount to be added to a stem cell culture media at least at about 37 ng/ml. For example, PDGF-AB may be present in a sufficient amount to be added to a stem cell culture media at least at about 38 ng/ml. For example, PDGF-AB may be present in a sufficient amount to be added to a stem cell culture media at least at about 39 ng/ml. For example, PDGF-AB may be present in a sufficient amount to be added to a stem cell culture media at least at about 40 ng/ml.

In an embodiment, the composition of the present disclosure further comprises EGF. For example, EGF may be present in a sufficient amount to be added to a stem cell culture media at about 0.1 ng/ml and 7 ng/ml. For example, EGF may be present in a sufficient amount to be added to a stem cell culture media at least at about 5 ng/ml.

In another example, EGF may be present in a sufficient amount to be added to a stem cell culture media at about 0.2 ng/ml and 3.2 ng/ml. In another example, EGF may be present in a sufficient amount to be added to a stem cell culture media at about 0.4 ng/ml and 1.6 ng/ml. For example, EGF may be present in a sufficient amount to be added to a stem cell culture media at least at about 0.2 ng/ml. For example, EGF may be present in a sufficient amount to be added to a stem cell culture media at least at about 0.3 ng/ml. For example, EGF may be present in a sufficient amount to be added to a stem cell culture media at least at about 0.4 ng/ml. For example, EGF may be present in a sufficient amount to be added to a stem cell culture media at least at about 0.5 ng/ml. For example, EGF may be present in a sufficient amount to be added to a stem cell culture media at least at about 0.6 ng/ml. For example, EGF may be present in a sufficient amount to be added to a stem cell culture media at least at about 0.7 ng/ml. For example, EGF may be present in a sufficient amount to be added to a stem cell culture media at least at about 0.8 ng/ml. For example, EGF may be present in a sufficient amount to be added to a stem cell culture media at least at about 0.9 ng/ml. For example, EGF may be present in a sufficient amount to be added to a stem cell culture media at least at about 1.0 ng/ml. For example, EGF may be present in a sufficient amount to be added to a stem cell culture media at least at about 1.1 ng/ml. For example, EGF may be present in a sufficient amount to be added to a stem cell culture media at least at about 1.2 ng/ml. For example, EGF may be present in a sufficient amount to be added to a stem cell culture media at least at about 1.3 ng/ml. For example, EGF may be present in a sufficient amount to be added to a stem cell culture media at least at about 1.4 ng/ml.

In an example, PDGF-BB, EGF and FGF2 are present in a sufficient amount to be added to stem cell culture media at least at about 3.2 ng/ml, 0.08 ng/ml and 0.002 ng/ml respectively. In an example, PDGF-BB, EGF and FGF2 are present in a sufficient amount to be added to stem cell culture media at least at about 9.6 ng/ml, 0.24 ng/ml and 0.006 ng/ml respectively. In an example, PDGF-BB, EGF and FGF2 are present in a sufficient amount to be added to stem cell culture media at least at about 16 ng/ml, 0.4 ng/ml and 0.02 ng/ml respectively. In an example, PDGF-BB, EGF and FGF2 are present in a sufficient amount to be added to stem cell culture media at least at about 32 ng/ml, 0.8 ng/ml and 0.01 ng/ml respectively.

In an example, the composition of the present disclosure may be packaged in or with a suitable solvent or in lyophilised form.

The cell culture medium and/or compositions disclosed herein may optionally be packaged in a suitable container with written instructions for a desired purpose, such as mixing of the composition with cell culture media to provide a specific concentration.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The present application claims priority from AU 2015900752 filed 4 Mar. 2015 and AU 2015900777 filed 5 Mar. 2015, the disclosures of which are incorporated herein by reference.

EXAMPLES

Example 1: Growth Factors in Cell Culture Medium

To assess serial propagation of mesenchymal lineage precursor cells (MPC) in human platelet lysate, cells were cultured in human platelet lysate for seven days before measuring cell proliferation. Platelet lysate was obtained from two separate suppliers (supplier A and supplier B). The platelet lysate percentage ranged from 0 to 10%. MPC proliferation at day seven is shown in FIG. 1. It was noted that the cell proliferation was highest when cells were grown in 10% human platelet lysate obtained from supplier B.

The concentrations (pg/ml) of growth factors EGF, FGF2, VEGF, PDGF-AA and PDGF-BB were measured in the human platelet lysate obtained from supplier A and B. The growth factor concentrations (pg/ml) are shown in Table 1. It was noted that supplier B had the highest concentration of EGF (8,036 pg/ml), the highest concentration of PDGF-BB (46,432 pg/ml) and the lowest concentration of FGF2 (199 pg/ml).

TABLE 1

| Analyte Sample | EGF pg/ml | FGF-2 pg/ml | VEGF pg/ml | PDGF-AA pg/ml | PDGF-BB pg/ml |
|---|---|---|---|---|---|
| Supplier A - lot 1 | 3,875 | 266 | 3,745 | 31,063 | 139,300 |
| Supplier A - lot 2 | 4,197 | 234 | 5,252 | 36,110 | 199,900 |
| Supplier B - lot 1 | 8,036 | 199 | 3,745 | 46,432 | 326,100 |
| Supplier A - lot 3 | 5,982 | 314 | 2,546 | 37,852 | 230,600 |

Example 2: The Effect of Growth Factors on Cell Proliferation

To assess the effect of growth factors in hPL on cell proliferation, cell populations were exposed to antibody antagonists of growth factors EGF, FGF2, VEGF, PDGF-AA and PDGF-BB.

Cell populations were exposed to either a single antibody antagonist, a combination of all antibody antagonists or an Ig antibody control. Antibodies were obtained from R&D systems and were added at saturating concentrations. After the addition of antibodies, cells were cultured for 5 days in 3% hPL (PLTMax) before measuring cell proliferation. The level of cell proliferation in each cell population exposed to the antibody antagonists was compared to the level of cell proliferation in cell populations exposed to the Ig control antibody.

Figure 2:
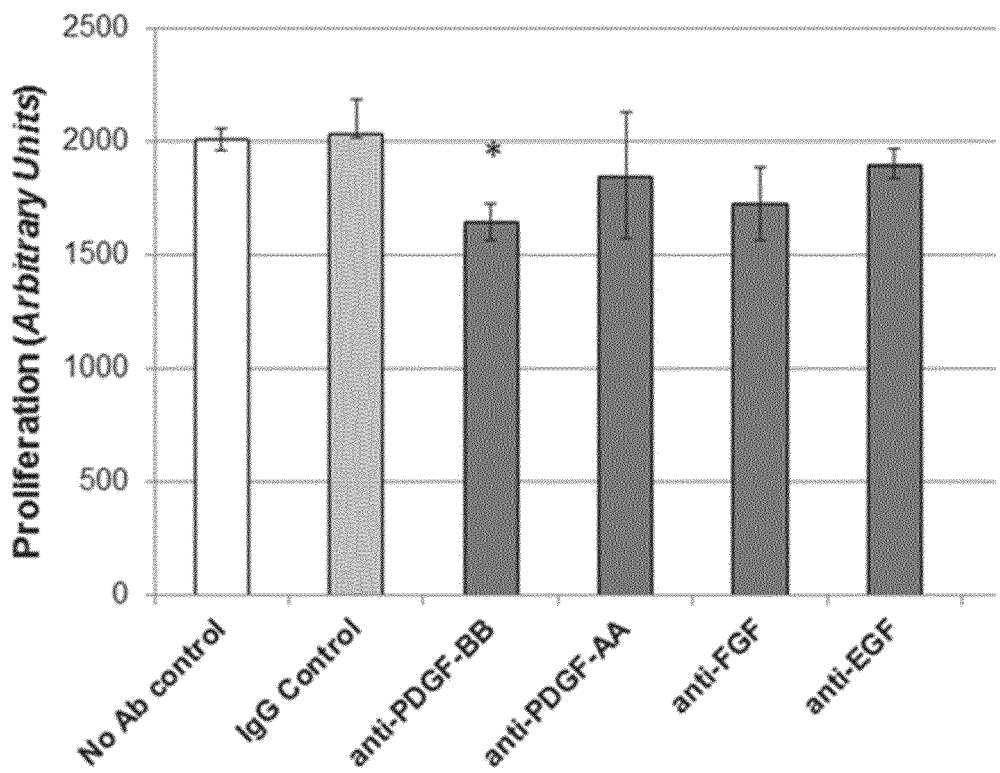
FIG. 2: Effect of antibody neutralisation of growth factors on MPC proliferation.

Antibody neutralisation of PDGF-BB was the only condition that resulted in a significant decline in MPC proliferation of the single anti-mitogen antibodies tested (FIG. 2).

The combination of all antibody antagonists resulted in almost complete suppression of cell proliferation (FIG. 2). Thus, the stimulation of cell proliferation by hPL is almost completely encompassed by the five growth factors examined in this initial experiment.

These results also demonstrate that one of the other growth factor(s) was contributing to PDGF-BB driven MPC proliferation.

Example 3: The Effect of Growth Factors on Cell Proliferation

Figure 3:
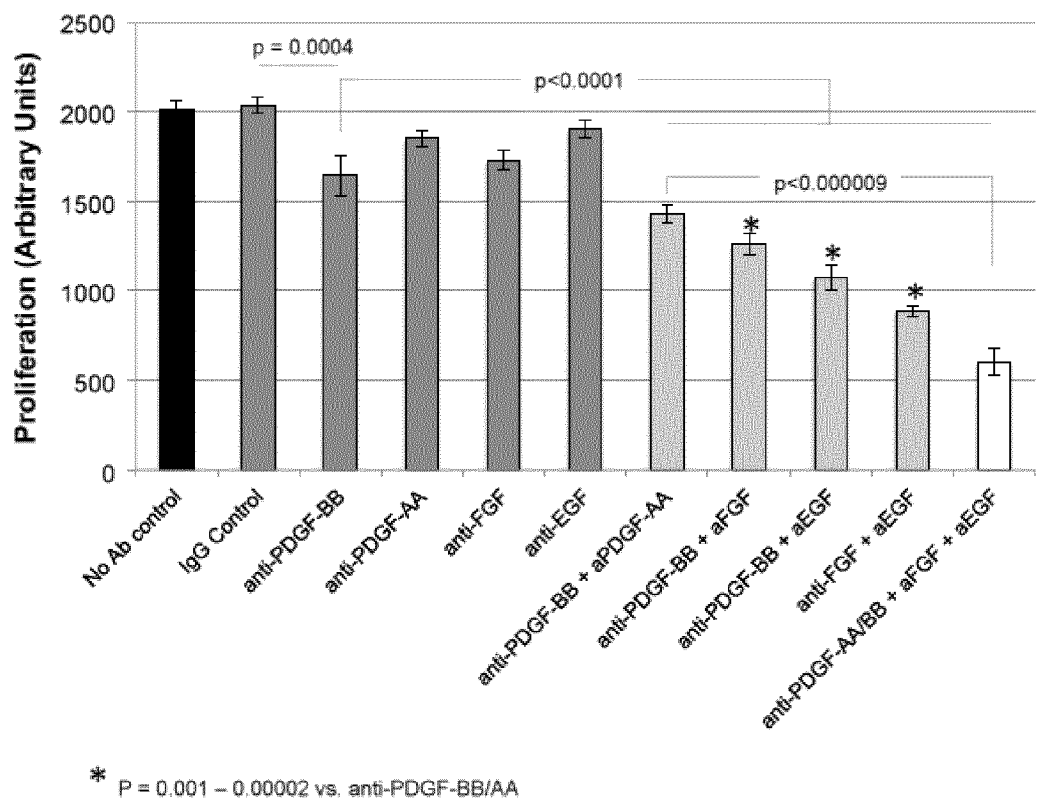
FIG. 3: Effect of combined antibody neutralisation of growth factors on MPC proliferation.

To assess which other growth factor(s) was contributing to PDGF-BB driven MPC proliferation, MPC cells were cultured with various combinations of antibodies as shown in FIG. 3.

After the addition of antibodies, cells were cultured for 5 days in 3% hPL (PLTMax) before measuring cell proliferation. The level of cell proliferation in each cell population exposed to the antibody antagonists was compared to the level of cell proliferation in cell populations exposed to an Ig control antibody and cell populations not exposed to an antibody (FIG. 3).

This study demonstrates that PDGF-BB, EGF and FGF2 stimulate MPC proliferation by hPL. Furthermore, PDGF-BB and EGF each act synergistically with FGF2 to promote cell proliferation. It was noted that the concentration of FGF2 in 3% hPL is approximately 6 pg/ml which is a sub-mitogenic dose.

As expected, no difference in cell proliferation was observed between cell populations cultured with the Ig control and cell populations not exposed to an antibody.

These data represent the basis for development of a chemically defined, fully humanised xeno-free cell culture medium in which MPC proliferation is driven by recombinant mitogens.

Example 4: Development of a Fetal Bovine Serum Free Cell Culture Medium

Starting basal cell culture mediums included alpha modified Eagle's minimum essential media (MEM) or StemSpan™.

The Alpha modification of Eagle's MEM with Earle's balanced salts, commonly referred to as Eagle's Alpha MEM, contains non-essential amino acids, sodium pyruvate, and additional vitamins. These modifications were first described for use in growing hybrid mouse and hamster cells (Stanners et al. Nat New Biol., 230, 52-54, 1971).

StemSpan™ is a fetal bovine serum free, hematopoietic cell expansion media available commercially from STEM-CELL Technologies. The composition of StemSpan™ has not been disclosed.

Compositions comprising PDGF-BB, EGF and FGF2 were added to each basal medium to the following concentrations:

PDGF-BB (3.2 ng/ml), EGF (0.08 ng/ml) and FGF2 (0.002 ng/ml)
PDGF-BB (9.6 ng/ml), EGF (0.24 ng/ml) and FGF2 (0.006 ng/ml)
PDGF-BB (16 ng/ml), EGF (0.4 ng/ml) and FGF2 (0.01 ng/ml)
PDGF-BB (32 ng/ml), EGF (0.8 ng/ml) and FGF2 (0.02 ng/ml)

Figure 4:
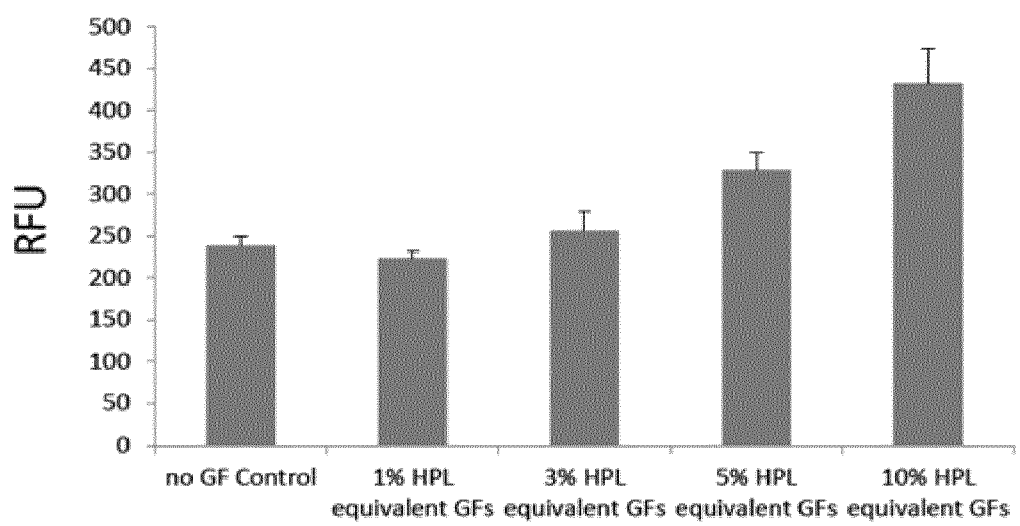
FIG. 4: MPC proliferation following cell culture on tissue culture plastic using Eagles Alpha MEM supplemented with varying concentrations of PDGF-BB, EGF and FGF2.
Figure 5:
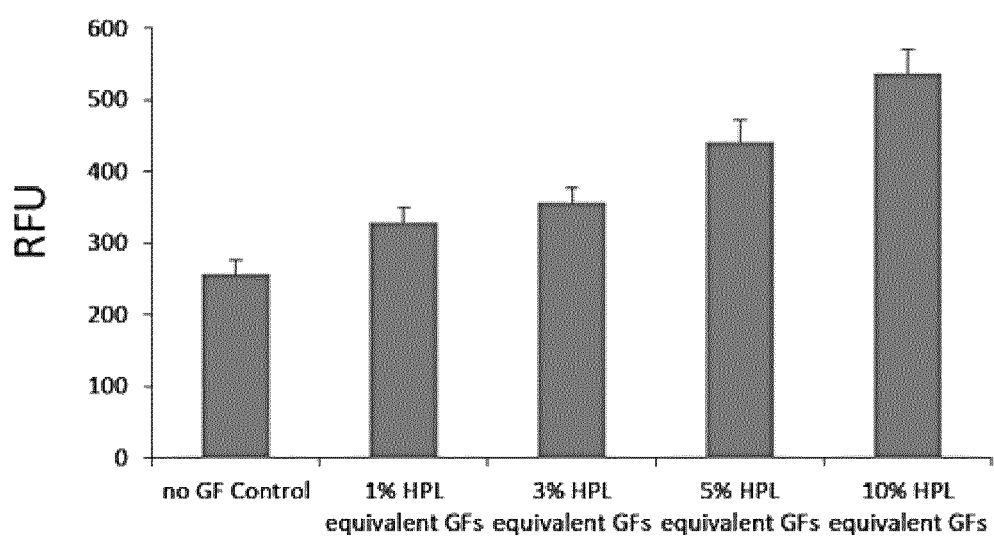
FIG. 5: MPC proliferation following cell culture on fibronectin using Eagles Alpha MEM supplemented with varying concentrations of PDGF-BB, EGF and FGF2.
Figure 6:
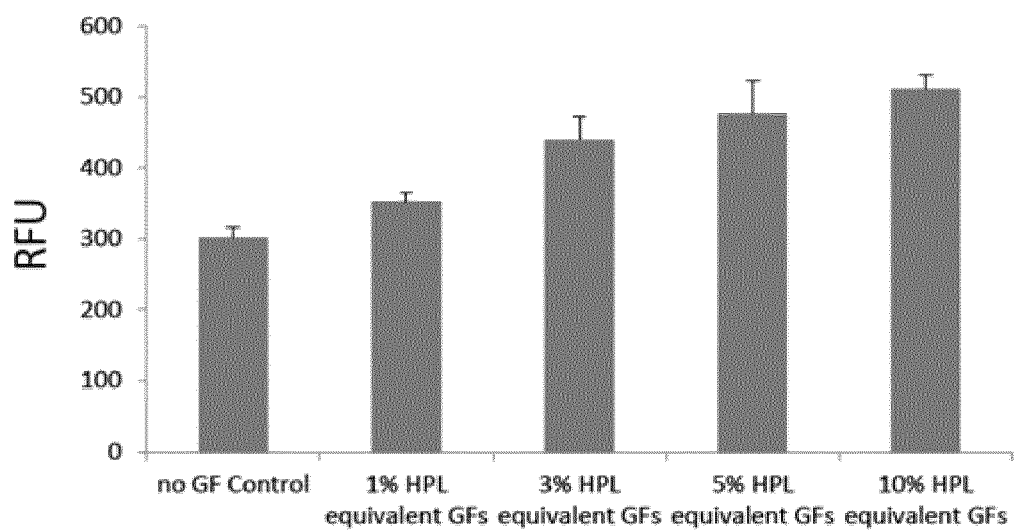
FIG. 6: MPC proliferation following cell culture on 3% hPL using Eagles Alpha MEM supplemented with varying concentrations of PDGF-BB, EGF and FGF2.
Figure 7:
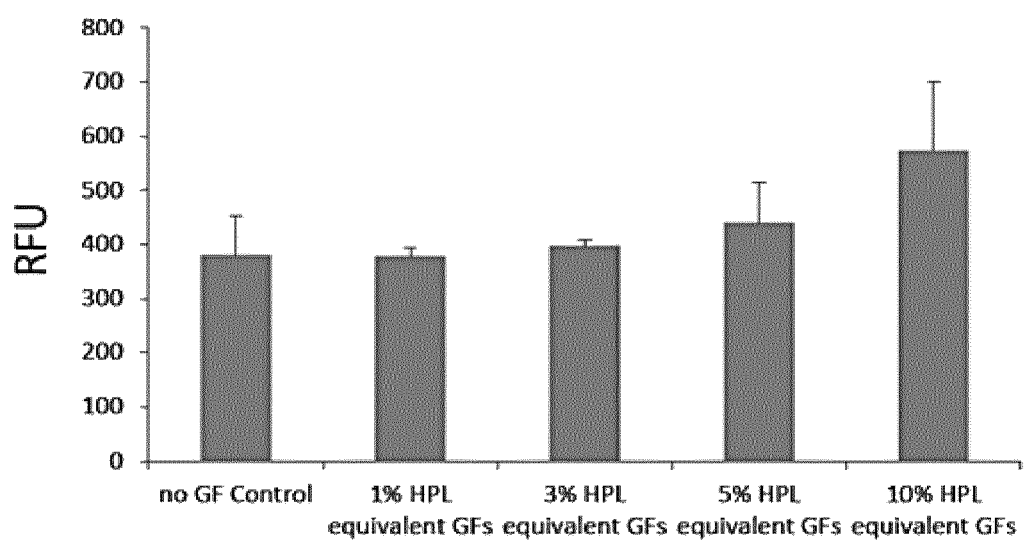
FIG. 7: MPC proliferation following cell culture on tissue culture plastic using StemSpan™ supplemented with varying concentrations of PDGF-BB, EGF and FGF2.
Figure 8:
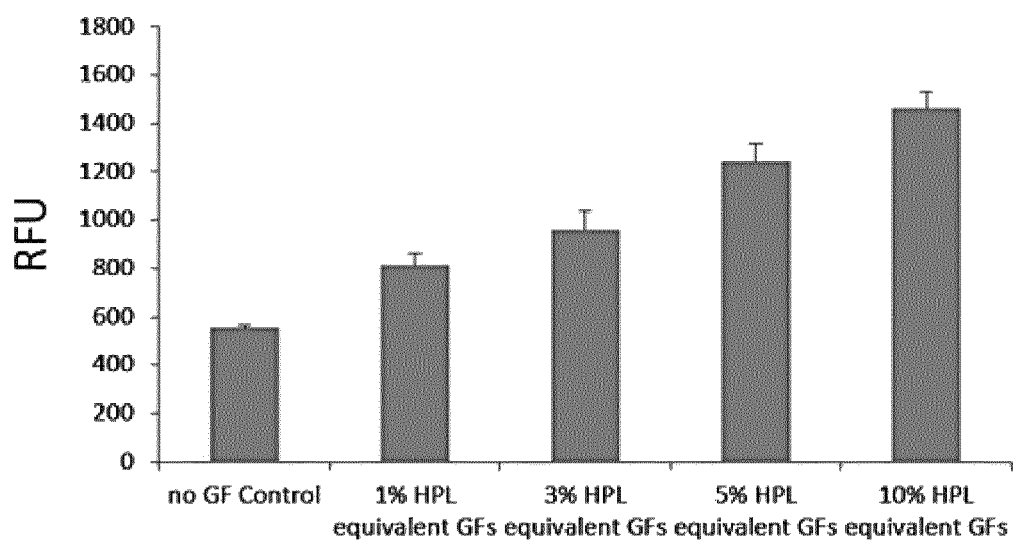
FIG. 8: MPC proliferation following cell culture on fibronectin using StemSpan™ supplemented with varying concentrations of PDGF-BB, EGF and FGF2.
Figure 9:
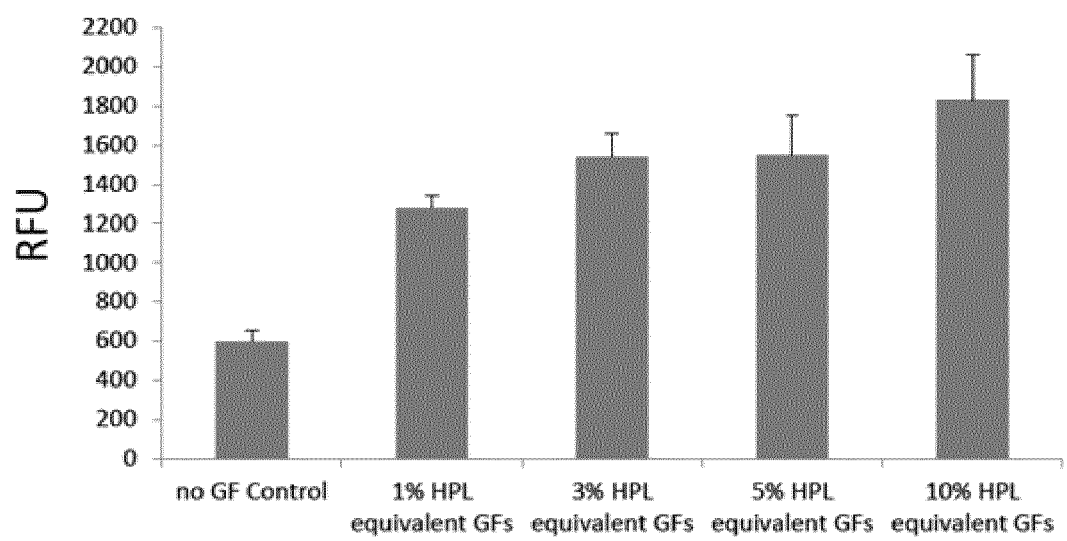
FIG. 9: MPC proliferation following cell culture on 3% hPL using StemSpan™ supplemented with varying concentrations of PDGF-BB, EGF and FGF2.

MSC populations were cultured in each of the above mediums (a-d) on tissue culture plastic (FIG. 4—Alpha MEM; FIG. 7—Stemspan™), fibronectin (FIG. 5—Alpha MEM; FIG. 8—Stemspan™) or 3% hPL (FIG. 6—Alpha MEM; FIG. 9—Stemspan™).

Cell proliferation in cell populations cultured in growth factor supplemented media was compared to cell proliferation in cell populations cultured in basal media without growth factors. The greatest increase in cell proliferation was observed in cells cultured in Alpha MEM or StemSpan™ basal media supplemented with PDGF-BB (32 ng/ml), EGF (0.8 ng/ml) and FGF2 (0.02 ng/ml).

Example 5: Xeno-Free Cell Culture

Cryopreserved human MPCs were thawed and seeded onto 96 well plates at 1,000 cells/well in xeno-free media supplemented with recombinant human growth factors or xeno-free media without growth factors.

Growth factors were provided in the following concentrations:

PDGF-BB (P)—10 ng/ml
EGF (E)—5 ng/ml
FGF2 (F)—1 ng/ml
PDGF, EGF, FGF2 (PEF)

Figure 10:
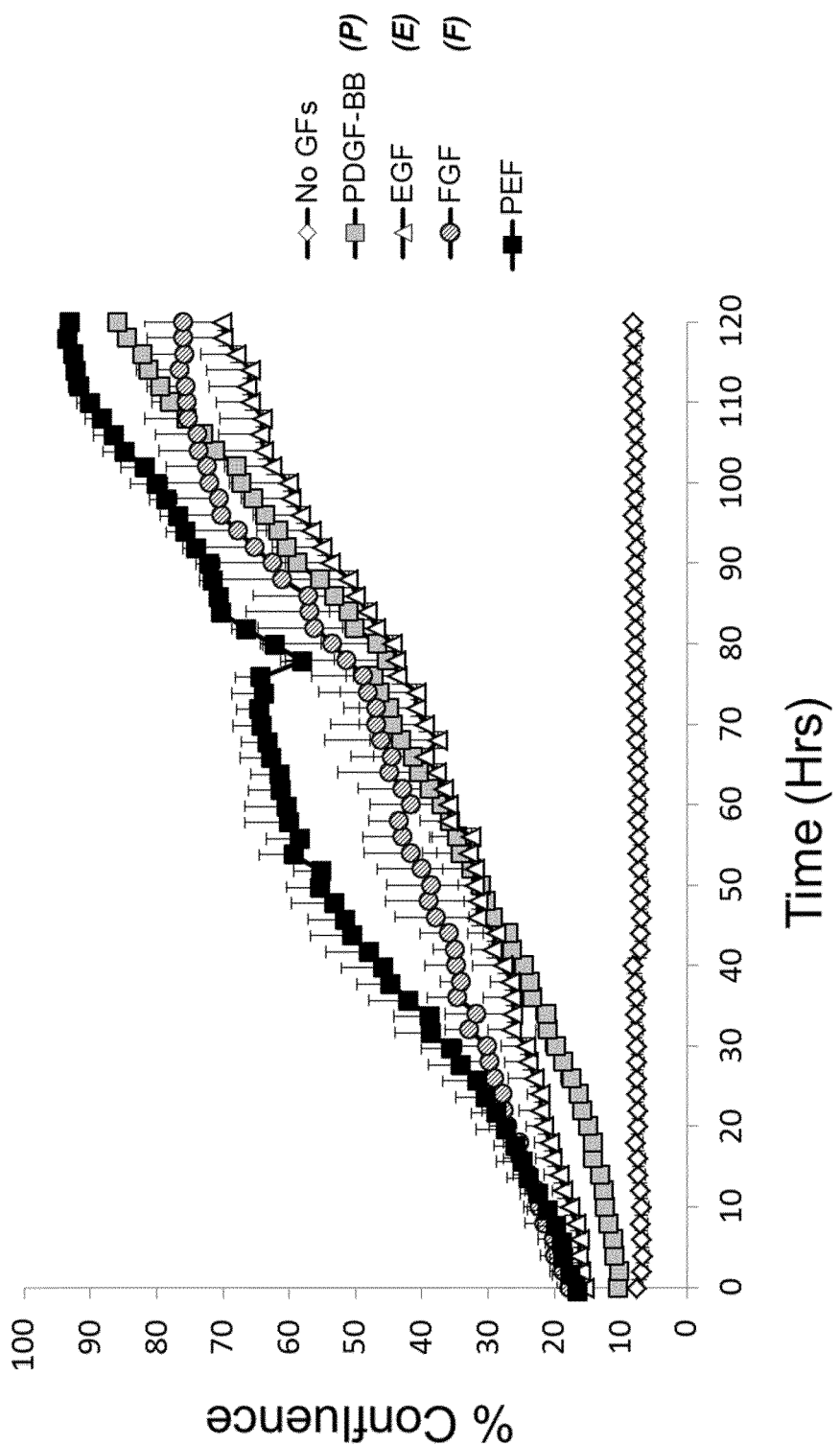
FIG. 10: Cell proliferation in media comprising PDGF (P), FGF (F), EGF (E) or a combination thereof (PEF).

Cultures were incubated for about 120 hours inside the IncuCyte Zoom live imaging microscope (Essen BioScience) fitted into a humidified NuAire incubator set at 5% $CO_2$, 35-37° C. Cells were simultaneously imaged every 6 hours to measure the level of confluence during the culture period. Proliferative kinetics were calculated as the percent of confluence over-time (FIG. 10).

Example 6: Comparison of Cytokine Levels in Cell Culture Medium from MPC

Figure 11:
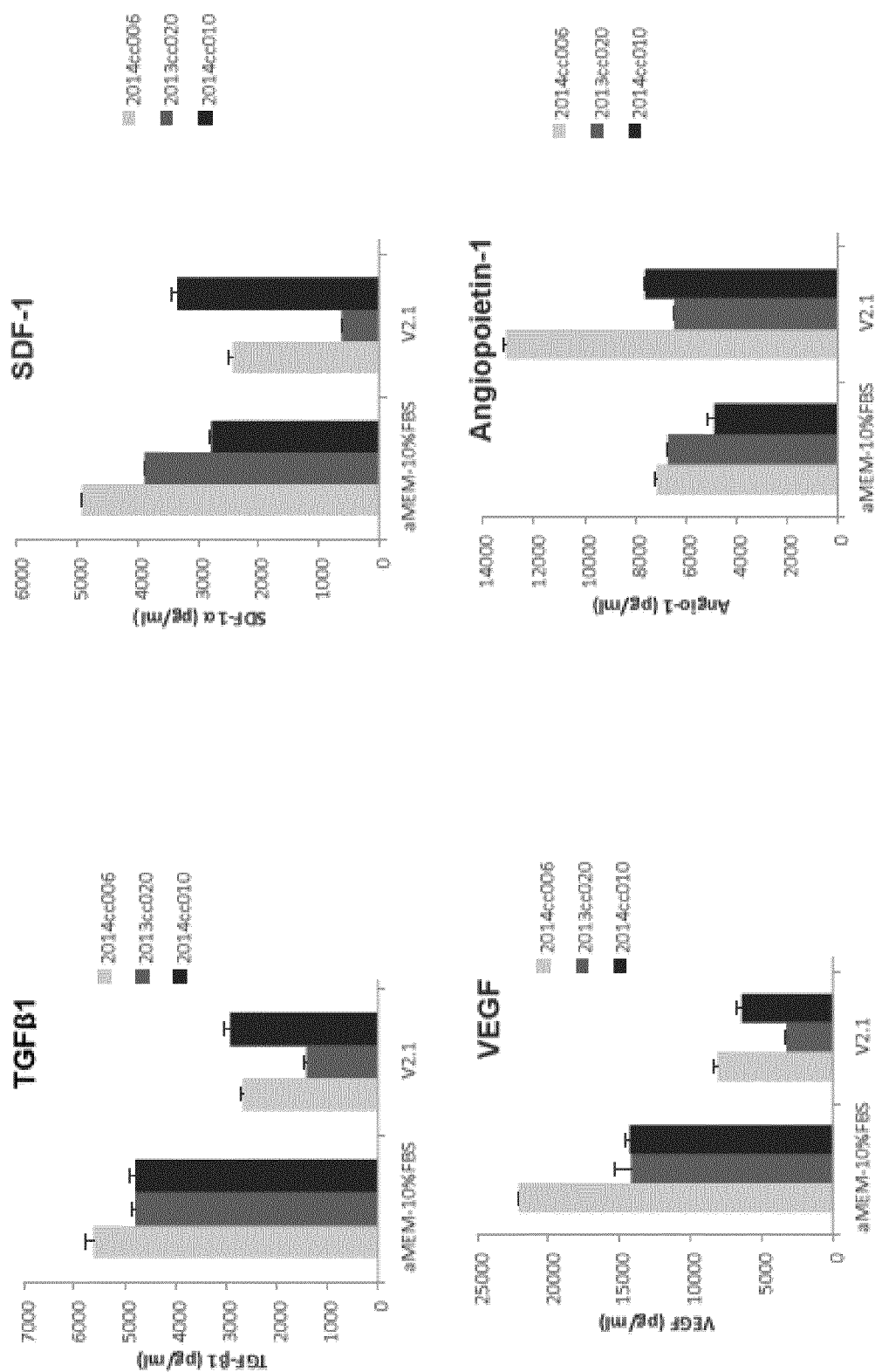
FIG. 11: Cytokine levels in cell culture medium after cell propagation.

MPC from 3 different donors were serially propagated in standard medium (alpha-MEM+10% FBS) or a fetal bovine serum free medium comprising alpha-MEM+3% human AB serum+ PDGF-BB, EGF and FGF2. Cytokine levels were measured in the cell culture medium after cell propagation (FIG. 11).

Ang1 levels were elevated in two of three donor cell populations grown in fetal bovine serum free medium. The Ang1:VEGF ratio increased in all donor cell populations grown in fetal bovine serum free medium.

The invention claimed is:

1. An in vitro method of cell culture, the method comprising:
    culturing a population of mesenchymal lineage precursor cells or stem cells in a fetal bovine serum free cell culture medium comprising platelet derived growth factor (PDGF), epidermal growth factor (EGF) and fibroblast growth factor 2 (FGF2), wherein the level of PDGF is 10 ng/ml or less, the level of EGF is 5 ng/ml or less, and the level of FGF2 is 1 ng/ml or less, wherein the method increases mesenchymal lineage precursor cell or stem cell proliferation.

2. The method of claim 1, wherein the level of FGF2 is between 2 pg/ml and 1 ng/ml.

3. The method of claim 1, wherein the level of FGF2 is 1 ng/ml.

4. The method of claim 1, wherein the PDGF is PDGF-BB.

5. The method of claim 4, wherein the level of PDGF-BB is 10 ng/ml.

6. The method of claim 1, wherein the level of EGF is between 0.08 ng/ml and 5 ng/ml.

7. The method of claim 1, wherein the level of EGF is between 3 ng/ml and 5 ng/ml.

8. The method of claim 1, wherein the cell culture medium comprises alpha-minimal essential medium.

9. The method of claim 1, wherein the cell culture medium maintains the mesenchymal lineage progenitor or stem cells in an undifferentiated state.

10. The method of claim 1, wherein culturing the population of mesenchymal lineage precursor or stem cells promotes cell proliferation relative to a control population of mesenchymal lineage precursor or stem cells cultured in a fetal bovine serum free cell culture medium without PDGF or FGF2.

11. The method of claim 1, wherein the mesenchymal lineage precursor cell or stem cell is a mesenchymal lineage precursor cell.

* * * * *